US010085675B2

(12) United States Patent
Nagasaki et al.

(10) Patent No.: US 10,085,675 B2
(45) Date of Patent: Oct. 2, 2018

(54) MEASUREMENT INFORMATION MANAGEMENT SYSTEM, MEASUREMENT APPARATUS, INFORMATION DEVICE, MEASUREMENT INFORMATION MANAGEMENT METHOD, AND MEASUREMENT INFORMATION MANAGEMENT PROGRAM

(71) Applicant: Seiko Epson Corporation, Shinjuku-ku (JP)

(72) Inventors: Shintaro Nagasaki, Hara-mura (JP); Yukari Araki, Nagahama (JP); Masanori Ojima, Kyoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 448 days.

(21) Appl. No.: 14/511,605

(22) Filed: Oct. 10, 2014

(65) Prior Publication Data
US 2015/0105677 A1    Apr. 16, 2015

(30) Foreign Application Priority Data

Oct. 11, 2013   (JP) ................................. 2013-213402

(51) Int. Cl.
*A61B 5/11*   (2006.01)
*A61B 5/024*  (2006.01)
(Continued)

(52) U.S. Cl.
CPC ........ *A61B 5/1118* (2013.01); *A61B 5/02438* (2013.01); *A61B 5/1112* (2013.01);
(Continued)

(58) Field of Classification Search
CPC . A61B 5/02438; A61B 5/1112; A61B 5/1118; A61B 5/681; A61B 5/7282;
(Continued)

(56) References Cited

U.S. PATENT DOCUMENTS 6,553,242 B1   4/2003 Sarussi
6,697,658 B2   2/2004 Al-Ali
(Continued)

FOREIGN PATENT DOCUMENTS

EP   1 421 896 A2   5/2004
EP   1 421 896 A3   8/2004
(Continued)

OTHER PUBLICATIONS

Extended European Search Report, dated Mar. 9, 2015, of the corresponding European Application No. 14188287.8; 9 pgs.
(Continued)

*Primary Examiner* — Navin Natnithithadha
(74) *Attorney, Agent, or Firm* — Kilpatrick Townsend & Stockton LLP

(57) ABSTRACT

A measurement information management system includes a measurement apparatus and an information device. The measurement apparatus may include a storage unit; a timepiece unit; a measurement unit which measures biological information indicative of a state of a user; a determination unit which determines whether the biological information meets a certain condition to thereby determine whether or not the state of the user is a certain state; a storage control unit which causes the storage unit to store a time at which the biological information is measured, when the biological information meets the condition; and a transmission unit which transmits information to the information device. The information device may include a display unit. Either the measurement apparatus or the information device may further include a position information measurement unit which measures a location. The display unit may display at least one of the time and the location.

13 Claims, 18 Drawing Sheets

(51) Int. Cl.
| | |
|---|---|
| *G04G 21/04* | (2013.01) |
| *G16H 10/60* | (2018.01) |
| *A61B 5/00* | (2006.01) |
| *G04G 21/02* | (2010.01) |
| *G06F 19/00* | (2018.01) |

(52) U.S. Cl.
CPC ............ *A61B 5/681* (2013.01); *A61B 5/7282* (2013.01); *A61B 5/742* (2013.01); *G04G 21/025* (2013.01); *G04G 21/04* (2013.01); *G06F 19/3418* (2013.01); *G06F 19/3481* (2013.01); *G16H 10/60* (2018.01)

(58) Field of Classification Search
CPC ...... A61B 5/742; G04G 21/025; G04G 21/04; G06F 19/322; G06F 19/3418; G06F 19/3481
USPC ................ 600/500–503, 481, 483, 513, 595
See application file for complete search history.

(56) References Cited

U.S. PATENT DOCUMENTS

| | | | |
|---|---|---|---|
| 7,171,251 B2 | 1/2007 | Sarussi et al. | |
| 7,507,207 B2 | 3/2009 | Sakai et al. | |
| 7,590,438 B2 | 9/2009 | Sarussi et al. | |
| 7,603,152 B2 | 10/2009 | Sarussi et al. | |
| 7,606,607 B2 | 10/2009 | Sarussi et al. | |
| 7,613,490 B2 | 11/2009 | Sarussi et al. | |
| 7,650,176 B2 | 1/2010 | Sarussi et al. | |
| 8,734,296 B1 | 5/2014 | Brumback et al. | |
| 8,784,271 B2* | 7/2014 | Brumback | A61B 5/0015 340/870.16 |
| 8,814,754 B2* | 8/2014 | Weast | G06F 1/163 482/1 |
| 8,903,671 B2 | 12/2014 | Park et al. | |
| 8,944,958 B1 | 2/2015 | Brumback et al. | |
| 8,974,349 B2* | 3/2015 | Weast | G06F 1/163 482/1 |
| 8,988,214 B2* | 3/2015 | Altman | G06F 19/3418 340/539.11 |
| 9,011,292 B2* | 4/2015 | Weast | G06F 19/3481 482/1 |
| 9,026,927 B2* | 5/2015 | Brumback | A61B 5/0015 715/764 |
| 9,044,136 B2* | 6/2015 | Luo | A61B 5/0002 |
| 9,113,841 B2* | 8/2015 | Amagai | A63B 21/00 |
| 9,141,087 B2* | 9/2015 | Brown | G04F 10/00 |
| 9,141,759 B2* | 9/2015 | Burich | G06F 19/3418 |
| 9,160,063 B2 | 10/2015 | Lowe, Jr. et al. | |
| 9,317,660 B2* | 4/2016 | Burich | G06F 19/3418 |
| 9,352,207 B2* | 5/2016 | Balakrishnan | A61B 5/7246 |
| 9,474,955 B2* | 10/2016 | Cobbett | G06F 1/163 |
| 9,504,414 B2* | 11/2016 | Coza | G06F 3/011 |
| 9,533,228 B2* | 1/2017 | Dugan | A63F 13/816 |
| 2003/0158692 A1 | 8/2003 | Tamada | |
| 2003/0229276 A1 | 12/2003 | Sarussi et al. | |
| 2007/0149871 A1 | 6/2007 | Sarussi et al. | |
| 2007/0293746 A1 | 12/2007 | Sarussi et al. | |
| 2008/0076988 A1 | 3/2008 | Sarussi et al. | |
| 2008/0076990 A1 | 3/2008 | Sarussi et al. | |
| 2008/0097228 A1 | 4/2008 | Aihara et al. | |
| 2009/0040231 A1 | 2/2009 | Sano et al. | |
| 2009/0247849 A1 | 10/2009 | McCutcheon et al. | |
| 2010/0217099 A1 | 8/2010 | LeBoeuf et al. | |
| 2010/0244574 A1 | 9/2010 | Nishino et al. | |
| 2010/0331145 A1 | 12/2010 | Lakovic et al. | |
| 2011/0125037 A1 | 5/2011 | Iijima et al. | |
| 2011/0213217 A1 | 9/2011 | McKenna et al. | |
| 2012/0083671 A1 | 4/2012 | Kato et al. | |
| 2012/0083674 A1 | 4/2012 | Hidai et al. | |
| 2012/0253484 A1* | 10/2012 | Burich | G06F 19/3418 700/91 |
| 2012/0253485 A1* | 10/2012 | Weast | G06F 1/163 700/91 |
| 2012/0254934 A1* | 10/2012 | McBrearty | G06F 19/3481 725/118 |
| 2012/0274508 A1* | 11/2012 | Brown | G04F 10/00 342/357.25 |
| 2013/0041590 A1* | 2/2013 | Burich | G06F 19/3418 702/19 |
| 2013/0053697 A1 | 2/2013 | Holl et al. | |
| 2013/0106603 A1* | 5/2013 | Weast | G06F 1/163 340/539.11 |
| 2013/0106684 A1* | 5/2013 | Weast | G06F 19/3481 345/156 |
| 2013/0110264 A1* | 5/2013 | Weast | G06F 19/3481 700/91 |
| 2013/0178750 A1 | 7/2013 | Sheehan et al. | |
| 2013/0190908 A1 | 7/2013 | Ellis et al. | |
| 2013/0196688 A1* | 8/2013 | Lu | G01S 19/19 455/456.1 |
| 2013/0197680 A1* | 8/2013 | Cobbett | G06F 1/163 700/91 |
| 2013/0197857 A1* | 8/2013 | Lu | G01S 19/19 702/141 |
| 2013/0217979 A1 | 8/2013 | Blackadar et al. | |
| 2013/0246021 A1* | 9/2013 | Ura | G06F 17/5009 703/2 |
| 2013/0274587 A1* | 10/2013 | Coza | A61B 5/6804 600/409 |
| 2013/0274904 A1* | 10/2013 | Coza | G06F 3/011 700/91 |
| 2014/0077945 A1* | 3/2014 | Amagai | A63B 21/00 340/539.11 |
| 2014/0172132 A1* | 6/2014 | Ura | G06F 19/3481 700/90 |
| 2014/0176335 A1* | 6/2014 | Brumback | A61B 5/0015 340/870.01 |
| 2014/0176346 A1* | 6/2014 | Brumback | A61B 5/0015 340/870.16 |
| 2014/0176422 A1* | 6/2014 | Brumback | A61B 5/0015 345/156 |
| 2014/0180595 A1* | 6/2014 | Brumback | A61B 5/0015 702/19 |
| 2014/0244009 A1* | 8/2014 | Mestas | A63B 24/0062 700/91 |
| 2014/0306884 A1 | 10/2014 | Sano et al. | |
| 2014/0336519 A1 | 11/2014 | Kaib et al. | |
| 2015/0031963 A1 | 1/2015 | Wright et al. | |

FOREIGN PATENT DOCUMENTS

| | | |
|---|---|---|
| JP | 2001-356849 A | 12/2001 |
| JP | 2008-251073 A | 10/2008 |
| JP | 2009-039157 A | 2/2009 |
| JP | 2011-036617 A | 2/2011 |
| JP | 2011-104234 A | 6/2011 |
| JP | 2012-075489 A | 4/2012 |
| JP | 2012-090975 A | 5/2012 |
| JP | 2013-111202 A | 6/2013 |
| WO | 2006-038628 A1 | 4/2006 |
| WO | 2012/008264 A1 | 1/2012 |

OTHER PUBLICATIONS

Kamijoh, Noboru, et al., "Energy trade-offs in the IBM Wristwatch computer," Wearable Computers, 2001; Proceedings. Fifth International Symposium 0 N Oct. 8-9, 2001; Piscataway, NJ, USA; IEEE, Oct. 8, 2001, pp. 133-140.

Narayanaswami, Chandra, et al., "Challenges and considerations for the design and production of a purpose-optimized body-worn wrist watch computer," Proceedings of SPIE, vol. 5443, Sep. 15, 2004, pp. 1-12.

Extended European search report, dated Apr. 23, 2015, of the corresponding European Application No. 14188087.2; 14 pages.

Non-Final Office Action in related U.S. Appl. No. 14/512,272, dated Feb. 7, 2017 (26 pages).

(56) References Cited

OTHER PUBLICATIONS

Non-Final Office Action in related U.S. Appl. No. 14/512,272, dated Aug. 3, 2017 (13 pages).

* cited by examiner

MEASUREMENT INFORMATION MANAGEMENT SYSTEM, MEASUREMENT APPARATUS, INFORMATION DEVICE, MEASUREMENT INFORMATION MANAGEMENT METHOD, AND MEASUREMENT INFORMATION MANAGEMENT PROGRAM

CROSS REFERENCE TO RELATED APPLICATIONS

The present application is based on and claims priority from Japanese Patent Application No. 2013-213402, filed Oct. 11, 2013, the disclosure of which is incorporated herein by reference.

BACKGROUND

1. Technical Field

The present invention relates to a measurement information management system, a measurement apparatus, an information device, a measurement information management method and a measurement information management program for measuring biological information.

2. Related Art

According to the related art, a measurement apparatus which measures biological information such as user's pulse rates is known (see, for example, JP-A-2012-75489).

The biological/exercise information detection and display apparatus of JP-A-2012-75489 acquires biological information such as user's pulse rate, exercise information and diet information and determines the state of the user based on the acquired information. Based on the result of the determination of the state of the user, a display character is decided and the decided display character is displayed on the display unit.

Meanwhile, it is recently demanded that human emotions are computerized, using a measurement apparatus which acquires biological information of the user, such as the biological/exercise information detection and display apparatus of JP-A-2012-75489, so that the information is utilized for activities of a private individual or corporation.

SUMMARY

A measurement information management system includes a measurement apparatus and an information device which communicates with the measurement apparatus. The measurement apparatus may include a storage unit; a timepiece unit which measures time; a biological information measurement unit which measures biological information indicative of a state of a user; a biological information determination unit which determines whether the biological information meets a predetermined biological information condition to thereby determine whether or not the state of the user is a predetermined state; a storage control unit which causes the storage unit to store a time at which the biological information is measured, when the biological information is determined as meeting the predetermined biological information condition; and a transmission unit which transmits transmission information to the information device, the transmission information comprising the time and the biological information that is measured at the time. The information device may include a display unit; and a display control unit. Either the measurement apparatus or the information device may further include a position information measurement unit which measures a location of the position information measurement unit. If the measurement apparatus has the position information measurement unit, the transmission information transmitted by the transmission unit further includes the location. If the information device has the position information measurement unit, the information device further includes an information device-side storage unit and an information device-side storage control unit which causes the information device-side storage unit to store the time transmitted from the measurement apparatus and the location that is measured at the time. The display control unit may cause the display unit to display at least one of the time and the location.

The biological information may include a pulse rate, and the predetermined biological information condition may be met when the pulse rate is equal to or above a predetermined threshold.

The predetermined state may relate to whether or not the user is exercising, or whether or not the user is exercising vigorously.

The biological information may include a pulse rate and information indicative of whether or not the user is exercising. The predetermined biological information condition may include the pulse rate being equal to or above a predetermined threshold when the user is not exercising. The predetermined state of the user may be an excited state.

If the information device includes the position information measurement unit, the system may further include a server which communicates with the information device, and the information device may further include an information device-side transmission unit which transmits the time and the location stored in the information device-side storage unit to the server. The server may include a server-side storage unit, and a server-side storage control unit which causes the server-side storage unit to store the time and the location transmitted from the information device.

Additionally or alternatively, the system may further include a server, and the transmission unit may transmit the transmission information to the information device via the server. The server may include a server-side storage unit which stores the transmission information, and a server communication unit which provides the transmission information, based on a request by the information device.

The information device may be a mobile phone.

The measurement apparatus may be an accessory that is worn by the user.

The biological information measurement unit may include a pulse rate monitor and/or an accelerometer.

BRIEF DESCRIPTION OF THE DRAWINGS

Exemplary embodiments will be described in more detail with reference to the accompanying drawings, wherein like numbers reference like elements, and in which.

DESCRIPTION OF EXEMPLARY EMBODIMENTS

Hereinafter, an embodiment of the invention will be described with reference to the drawings.

Figure 1:
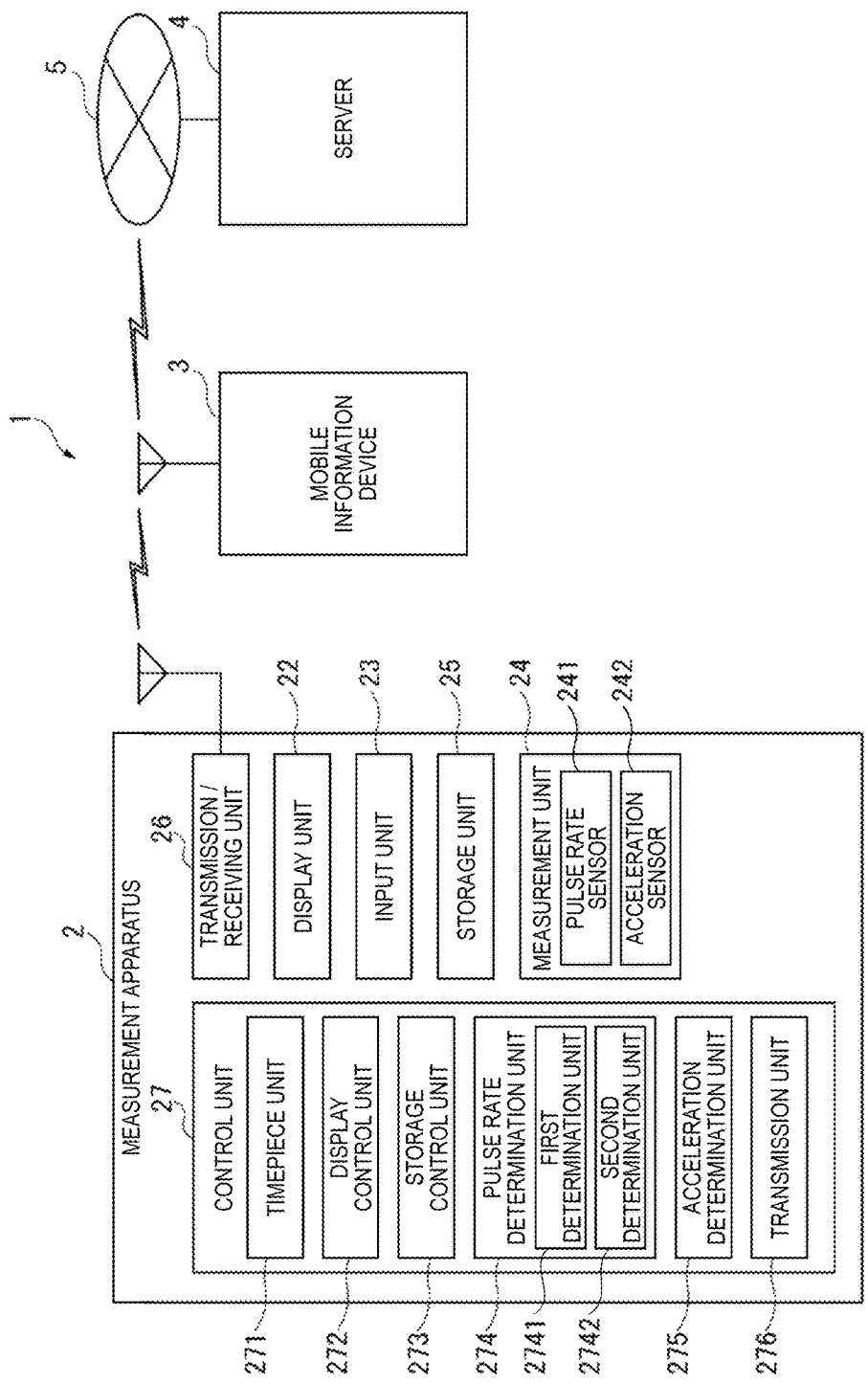
FIG. 1 is a block diagram showing the configuration of a measurement information management system according to an embodiment.

FIG. 1 is a block diagram showing the configuration of a measurement information management system 1 according to this embodiment.

As shown in FIG. 1, the measurement information management system 1 includes a measurement apparatus 2, a mobile information device 3, and a server 4 connected to a network 5.

Figure 2:
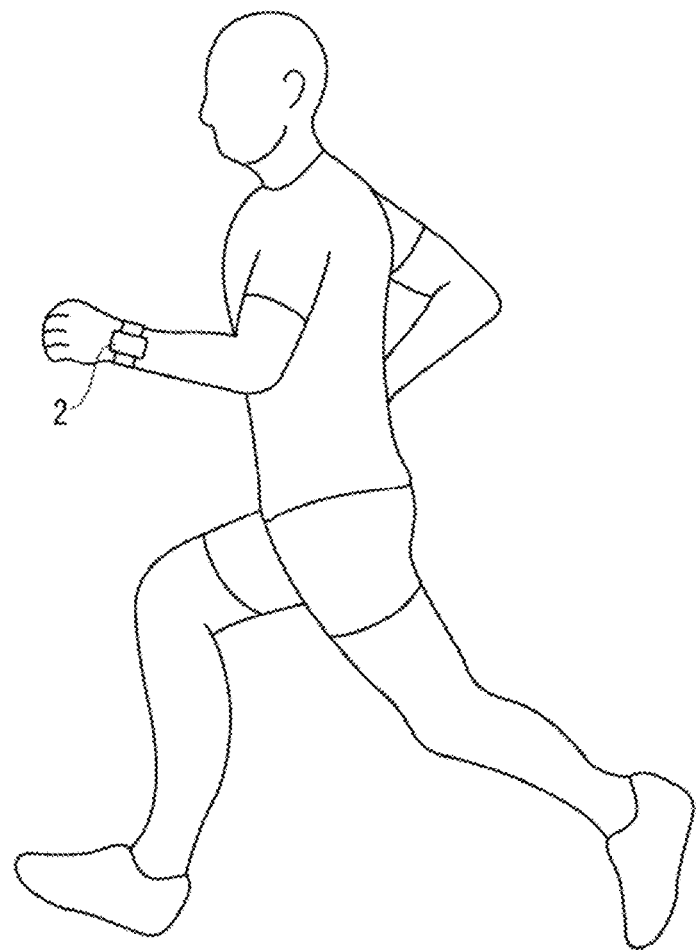
FIG. 2 shows the state where a measurement apparatus according to an embodiment is mounted on a user.

In some embodiments, the measurement apparatus 2 is a wristwatch-type apparatus, which is worn by the user for use as shown in FIG. 2 and measures time, pulse rate, acceleration and the like. However, the measurement apparatus 2 is not limited to a wristwatch type and may be in the form of, for example, spectacles, headset, hat, helmet, glove or the like. The measurement apparatus 2 can be in any form that enables measurement of time, pulse rate, and acceleration. The mobile information device 3 is a portable mobile information device, for example, a mobile phone or smartphone (multifunction mobile phone) or the like. To simplify the explanation, the mobile information device 3 is assumed as a smartphone. In this embodiment, when using the measurement apparatus 2, the user wears the measurement apparatus 2 and also carries the mobile information device 3.

Wireless communication is carried out between the measurement apparatus 2 and the mobile information device 3. The measurement apparatus 2 transmits a result of measurement to the mobile information device 3. The mobile information device 3 is wirelessly connected to the network 5 and transmits the result of measurement received from the measurement apparatus 2, to the server 4 via the network 5.

Configuration of Measurement Apparatus

Figure 3:
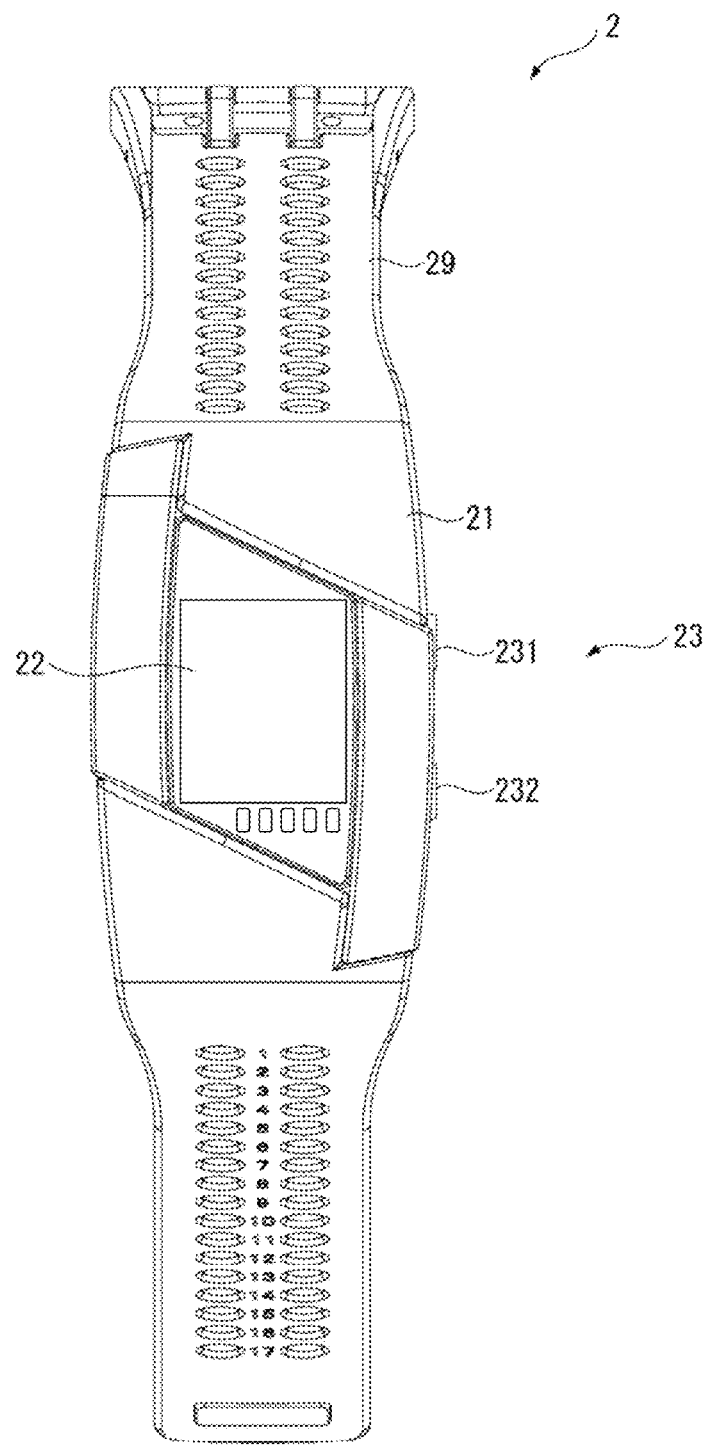
FIG. 3 is a front view showing the appearance of the measurement apparatus.

FIG. 3 is a front view showing the appearance of the measurement apparatus 2.

The measurement apparatus 2 has a casing 21 with a wristwatch-type appearance. A band 29 which allows the casing 21 to be worn on the user's wrist is provided on the casing 21. The measurement apparatus 2 further includes a display unit 22 provided on the front of the casing 21, and an input unit (operation unit) 23 having buttons 231, 232 provided on a lateral side of the casing 21.

In addition, the measurement apparatus 2 includes a measurement unit 24, a storage unit 25, a transmission/receiving unit 26 and a control unit 27, as shown in FIG. 1, inside the casing 21.

The display unit 22 is made up of a display panel such as a liquid crystal panel, organic EL (electro-luminescence) panel, or electrophoretic panel. On the display unit 22, the result of measurement of pulse rate or the like is displayed under the control of the control unit 27, described later.

The input unit 23 has the button 231, 232 and outputs an operation signal corresponding to a button pressed by the user, to the control unit 27.

The measurement unit 24 has a pulse rate sensor (biological information measurement unit) 241 and an acceleration sensor (exercise information measurement unit) 242 and outputs measurement signals from the respective sensors 241, 242 to the control unit 27.

Figure 4:
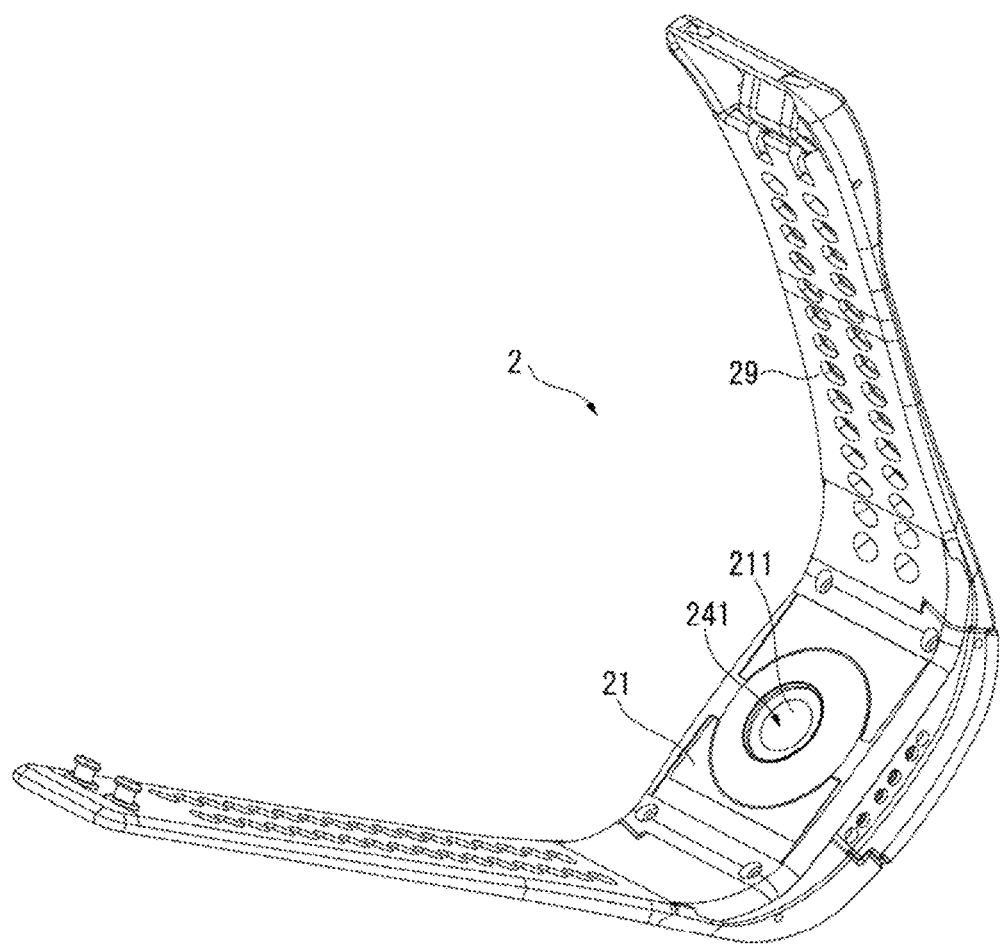
FIG. 4 is a backside view showing the appearance of the measurement apparatus.

On the back side of the casing 21, a transparent window 211 is provided, as shown in FIG. 4. The pulse rate sensor 241 is located behind this window 211 (on the inner side of the casing 21).

The pulse rate sensor 241 measures a pulse rate (which is an example of "biological information"). The pulse rate sensor 241 is made up of a photoelectric sensor having a light emitting element such as an LED (light emitting diode), for example, and a light receiving element such as a photodiode. In such a pulse rate sensor 241, with the measurement apparatus 2 worn on the wrist, light is cast through the user's skin from the light emitting element, and a change in the amount of light that arrives via a blood vessel of the user and is received by the light receiving element is detected. Thus, a pulse is detected. That is, the light cast on the user is partly absorbed in the blood vessel and the absorption rate in the blood vessel varies due to the influence of pulsation, resulting in a change in the amount of light that reaches the light receiving element. By analyzing the temporal change in the amount of light detected by the light receiving element, that is, the pulse, it is possible to measure the pulse rate. This is described in more detail in the present assignee's co-pending application Ser. No. 14/463,519, client reference number J0173922US01, titled "Heart Rate Monitor," filed Aug. 19, 2014, which is hereby incorporated by reference.

While a photoelectric sensor as the pulse rate sensor 241 is described as one exemplary embodiment, the invention is not limited thereto. The pulse rate sensor may additionally or alternatively include any appropriate sensor, such as an ultrasonic sensor which detects the contraction of a blood vessel with ultrasonic waves and thus measures the pulse rate, or a piezoelectric element or the like which provides a microcurrent from an electrode to flow through the user's body and thus detects the pulse rate.

The acceleration sensor 242 measures acceleration (which is one example of "exercise information") of the measurement apparatus 2, i.e. motion of the user's wrist, which is indicative of exercise.

The storage unit 25 may include a flash memory or the like, and stores various programs and information (user's date of birth, sex, physical information and the like) that are necessary for measurement. In addition, the storage unit 25 stores the information or the like measured by the measurement unit 24.

The transmission/receiving unit 26 is a communication module which wirelessly communicates with an external device such as the mobile information device 3. The transmission/receiving unit 26 transmits the information inputted from the control unit 27 to an external device with which communication connection is established, and also outputs the information received from the external device to the control unit 27. A module conformable to the Bluetooth (registered trademark) standard can be given as an example of the transmission/receiving unit 26.

The control unit 27 is configured to control the operation of the measurement apparatus 2 and includes an arithmetic unit such as a CPU (central processing unit). The control unit 27 functions as a timepiece unit 271 (i.e. a clock), a display control unit 272, a storage control unit 273, a pulse rate determination unit 274, an acceleration determination unit 275, and a transmission unit 276, as the CPU executes a program stored in the storage unit 25.

The timepiece unit 271 measures current time, such as with an oscillation signal (reference signal: 1 Hz) outputted from a crystal oscillator.

The display control unit 272 controls the operation of the display unit 22 and causes the operation state of the measurement apparatus 2 and the result of measurement or the like to be displayed.

The pulse rate determination unit (biological information determination unit) 274 determines whether the pulse rate measured by the pulse rate sensor 241 meets a predetermined pulse rate condition (biological information condition). Specifically, the pulse rate determination unit 274 has a first determination unit 2741 and a second determination unit 2742.

The first determination unit 2741 determines whether the pulse rate is equal to or above a first threshold (predetermined threshold) or not. The first threshold is set to a reference value that enables determination that the user's pulse rate is higher than a normal resting heart rate. The first threshold is set, for example, at 70 beats per minute (70 bpm).

The second determination unit 2742 determines whether the pulse rate is equal to or above a second threshold that has a higher value than the first threshold, or not. The second threshold is set to a reference value that enables determination that the user's pulse rate is significantly higher than the normal resting heart rate. The second threshold is set, for example, at 100 beats per minute (100 bpm).

The first threshold and the second threshold can be freely set by the user by operating the input unit 23 or by remote operation with the mobile information device 3. Alternatively, the first threshold and the second threshold can be set automatically by the control unit 27, based on an average value of pulse rates stored in the storage unit 25.

The acceleration determination unit (exercise information determination unit) 275 determines whether the acceleration measured by the acceleration sensor 242 meets a predetermined acceleration condition (exercise information condition). The predetermined acceleration condition is a condition for determining that the user is in a normally active state, as opposed to an exercising state.

The storage control unit 273 determines an excited state or a vigorously exercising state (overloaded state) of the user if the user is in such states, and causes the storage unit 25 to store the pulse rate measured by the pulse rate sensor 241, measurement time information corresponding to the measurement time when the measurement is carried out, and the fact that the user is in the state. In some embodiments, the measurement time information indicates the measurement time (hour-minute-second) when the measurement is carried out.

When the user is in an excited state, the pulse rate tends to be higher than normal even though the user is in a normally active state (not exercising). Therefore, if the acceleration determination unit 275 determines that the acceleration meets the predetermined acceleration condition and the pulse rate determination unit 274 determines that the pulse rate is equal to or above the first threshold, the storage control unit 273 determines that the user is in an excited state and causes the storage unit 25 to store the pulse rate, the measurement time information, and the fact that the user is in the excited state. In other words, the storage control unit 273 determines that the user is excited when he or she has a high pulse rate but is not exercising.

When the user is in a vigorously exercising state, the pulse rate tends to be significantly higher than usual. Therefore, if the acceleration determination unit 275 determines that the acceleration does not meet the predetermined acceleration condition and the pulse rate determination unit 274 determines that the pulse rate is equal to or above the second threshold, the storage control unit 273 determines that the user is in a vigorously exercising state and causes the storage unit 25 to store the pulse rate, the measurement time information, and the fact that the user is in the vigorously exercising state.

If the pulse rate is not significantly higher than usual (for example, above approximately 90 beats per minute) while the user is in an exercising state, the storage control unit 273 causes the storage unit 25 not to store the pulse rate, the measurement time information and the result of the determination of the state of the user of the state of the user.

The transmission unit 276 transmits the pulse rate, the measurement time information and the result of the determination of the state of the user stored in the storage unit 25 to the mobile information device 3. The information transmitted from the transmission unit 276 is sometimes referred to herein as the transmission information.

Configuration of Mobile Information Device

Figure 5:
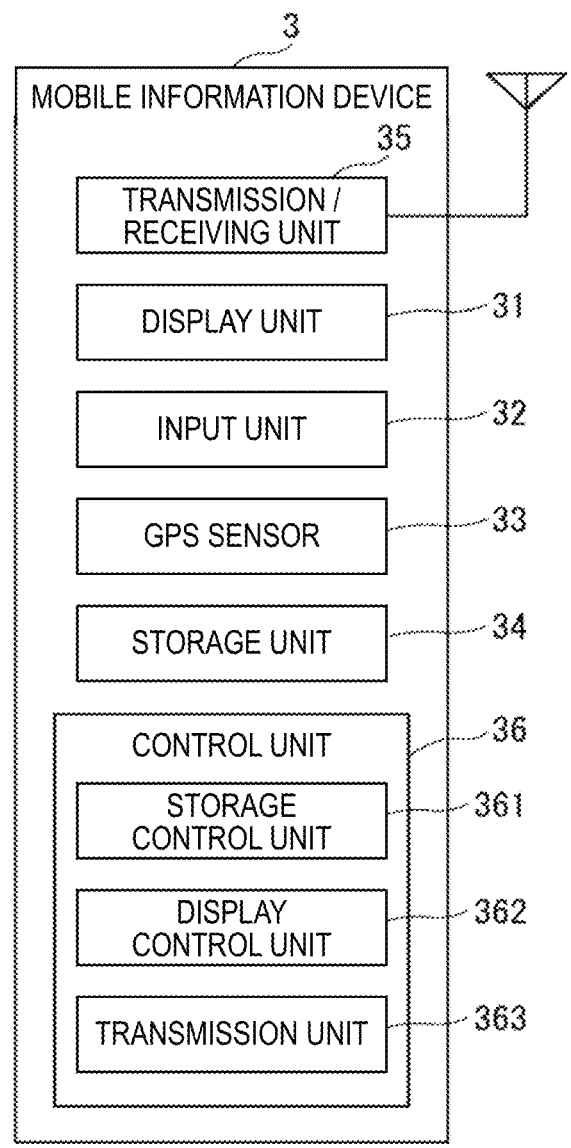
FIG. 5 is a block diagram showing the configuration of a mobile information device according to an embodiment.

FIG. 5 is a block diagram showing the configuration of the mobile information device 3.

As shown in FIG. 5, the mobile information device 3 has a display unit 31, an input unit 32, a GPS (global positioning system) sensor (position information measurement unit) 33, a storage unit (information device-side storage unit) 34, a transmission/receiving unit 35, and a control unit 36.

The display unit 31 has a display panel and displays a predetermined image under the control of the control unit 36.

The input unit 32 has a button provided on the outer surface of the casing of the mobile information device 3 or a touch panel provided corresponding to the display area of an image on the display unit 31, or the like. The input unit 32 outputs an operation signal corresponding to the user's input operation on the button or the touch panel, to the control unit 36.

The GPS sensor 33 receives GPS signals (satellite signals) from at least three GPS satellites, of plural GPS satellites orbiting around the earth, and measures position information of the current location of the mobile information device 3 (in other words, the current location of the user). If GPS signals are received from four or more GPS satellites, the altitude of the current location as well as the position information of the current location is measured.

The storage unit 34 is made up of an HDD (hard disk drive), flash memory or the like, and stores various programs and information that are necessary for the operation of the mobile information device 3. The storage unit 34 stores, for example, the pulse rate, the measurement time information and the result of the determination of the state of the user transmitted from the measurement apparatus 2, and the position information measured by the GPS sensor 33.

The transmission/receiving unit (information receiving unit) 35 is a communication module which communicates with an external device such as the measurement apparatus 2 and with the network 5 or the like. The transmission/receiving unit 35 transmits and receives information to and from the external device and the network 5 or the like under the control of the control unit 36.

The control unit 36 is configured to control the operation of the mobile information device 3 and is made up of a CPU. The control unit 36 functions as a storage control unit (information device-side storage control unit) 361, a display control unit 362, and a transmission unit (information device-side transmission unit) 363 as the CPU executes a measurement information management program stored in the storage unit 34. The measurement information management program is, for example, acquired from outside by the transmission/receiving unit 35 and stored in the storage unit 34.

The storage control unit 361 causes the storage unit 34 to store the pulse rate, the measurement time information and the result of the determination of the state of the user transmitted from the measurement apparatus 2 and received by the transmission/receiving unit 35, and the position information measured by the GPS sensor 33 corresponding to the measurement time information (in other words, the current location of the user). The position information corresponding to the measurement time information is position information measured at the same time as the measurement time. That is, the storage control unit 361 causes the storage unit 34 to store the pulse rate, the measurement time information and the result of the determination of the state of the user transmitted from the measurement apparatus 2, and the position information of the place where the pulse rate is measured.

The transmission unit 363 transmits the pulse rate, the measurement time information, the result of the determination of the state of the user and the position information stored in the storage unit 34, to the server 4.

The display control unit 362 generates an event confirmation screen 37 showing the pulse rate, the measurement time information, the result of the determination of the state of the user and the position information stored in the storage unit 34, and causes the display unit 31 to display the event confirmation screen 37.

Figure 6:
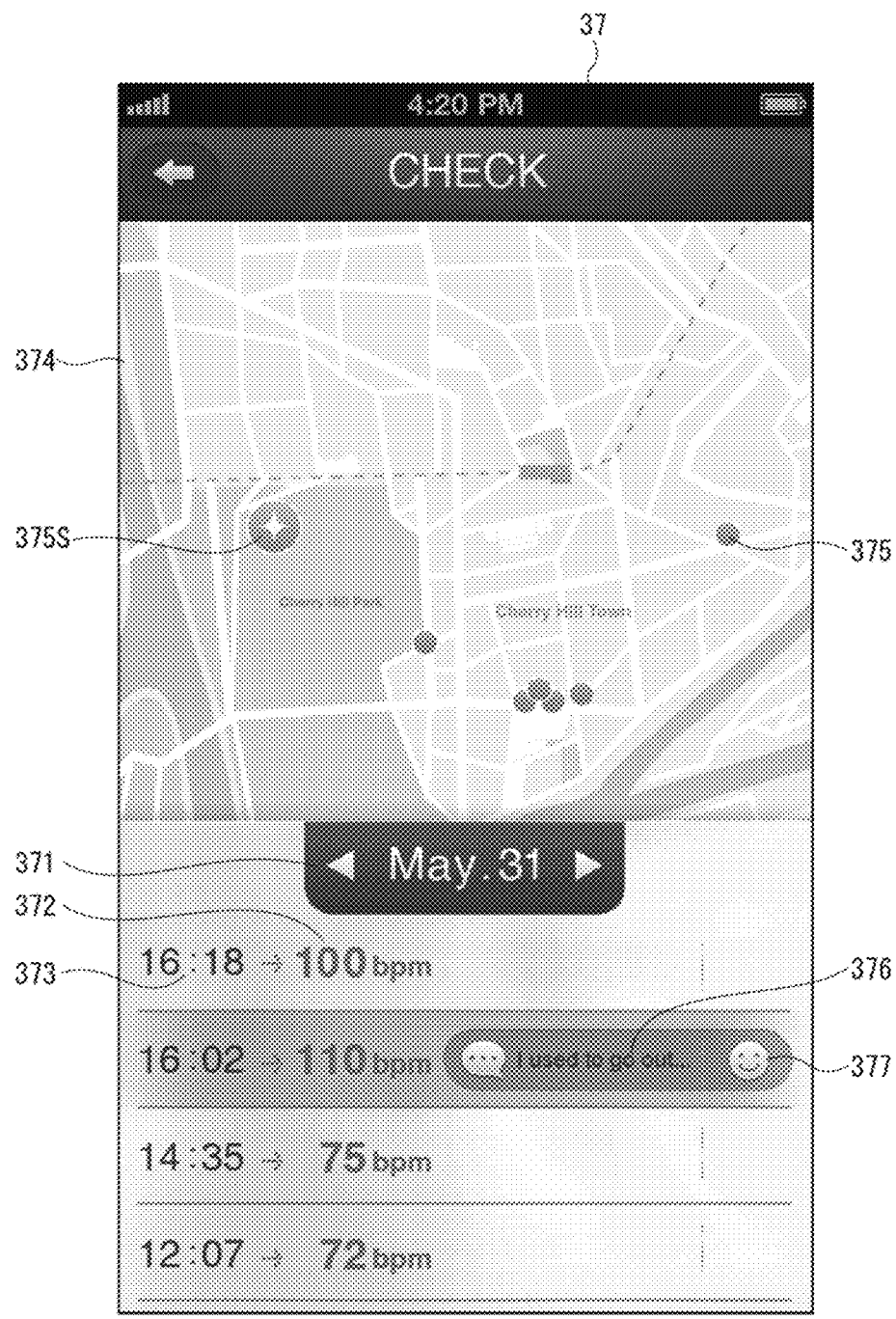
FIG. 6 shows an example of an event confirmation screen according to an embodiment.

FIG. 6 shows an example of the event confirmation screen 37.

In the event confirmation screen 37, a date 371 when the measurement is carried out, a pulse rate 372 and measurement time information 373 stored in the storage unit 34, and map information 374 indicating position information are shown. While only hours and minutes are shown here as the measurement time information 373, an hour-minute-second indication or an hour-only indication may also be shown.

The pulse rate 372 and the measurement time information 373 are shown in the form of a list by each day when measurement is carried out. In the map information 374, a place indicated by the position information corresponding to the pulse rate 372 and the measurement time information 373 is shown by a marker 375 on a map. That is, the marker 375 is an event marker indicating the place where an event is generated, on the map.

The result of the determination of the state of the user on whether the user is in an excited state or in a vigorously exercising state is expressed, for example, by the color of the pulse rate 372, the measurement time information 373, and the marker 375. For example, an excited state is expressed by a cold color, and a vigorously exercising state is expressed by a warm color.

That is, by browsing the event confirmation screen 37, the user can ascertain the time and place where the user is in an excited state and the pulse rate at that time, and the time and place where the user is in a vigorously exercising state and the pulse rate at that time.

If the user operates the input unit 32 to select one of the pulse rates 372 and the measurement time information 373 from the list, a marker 375S corresponding to the pulse rate 372 and the measurement time information 373 that are selected is shown in an enlarged manner. Thus, the place where the selected pulse rate 372 is measured can be clearly displayed on the map.

A comment 376 and an emoticon 377 can be displayed with the pulse rate 372 and the measurement time information 373. The comment 376 and the emoticon 377 can be input by the user operating the input unit 32, e.g. by typing on a touch-screen keyboard.

Specifically, as the user operates the input unit 32 to select one of the markers 375 shown on the map or to select one of the pulse rates 372 and the measurement time information 373 from the list, a comment input icon and an emoticon input icon, not shown, are displayed at the right end of the pulse rate 372 and the measurement time information 373 that are selected.

Then, as the user operates the input unit 32 to select the comment input icon, a comment input section, not shown, is displayed. The user then can input the comment 376 by operating the input unit 32 to input a comment in the comment input section.

Figure 7:
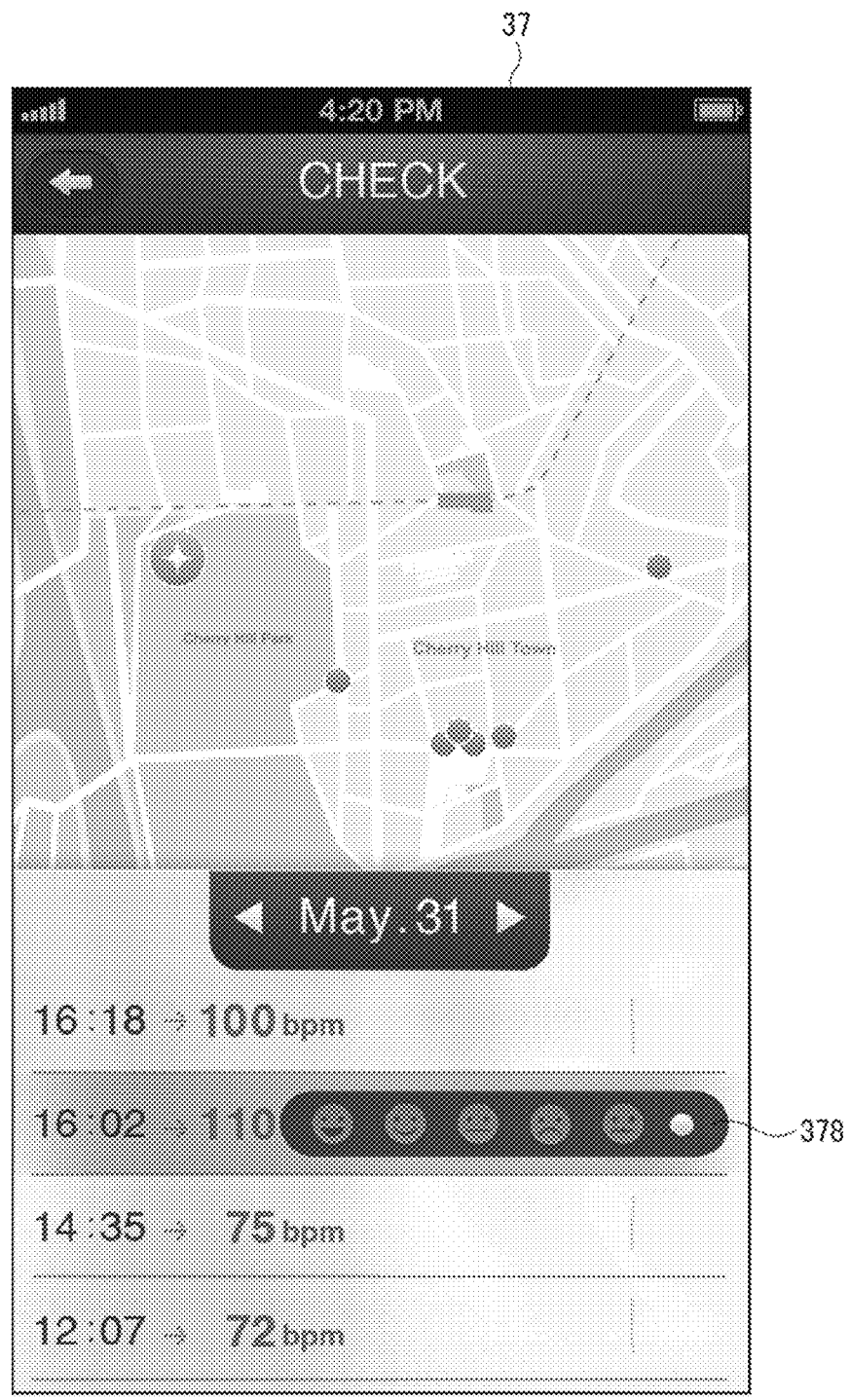
FIG. 7 shows an example of the event confirmation screen.

Also, as the user operates the input unit 32 to select the emoticon input icon, an emoticon selection image 378 including plural kinds of emoticons is displayed, as shown in FIG. 7. The user then can input the emoticon 377 by operating the input unit 32 to select one of the emoticons.

Thus, the comment and the emotion at the time of measurement can be left as a memo with respect to the pulse rate 372 and the measurement time information 373.

Configuration of Server

Figure 8:
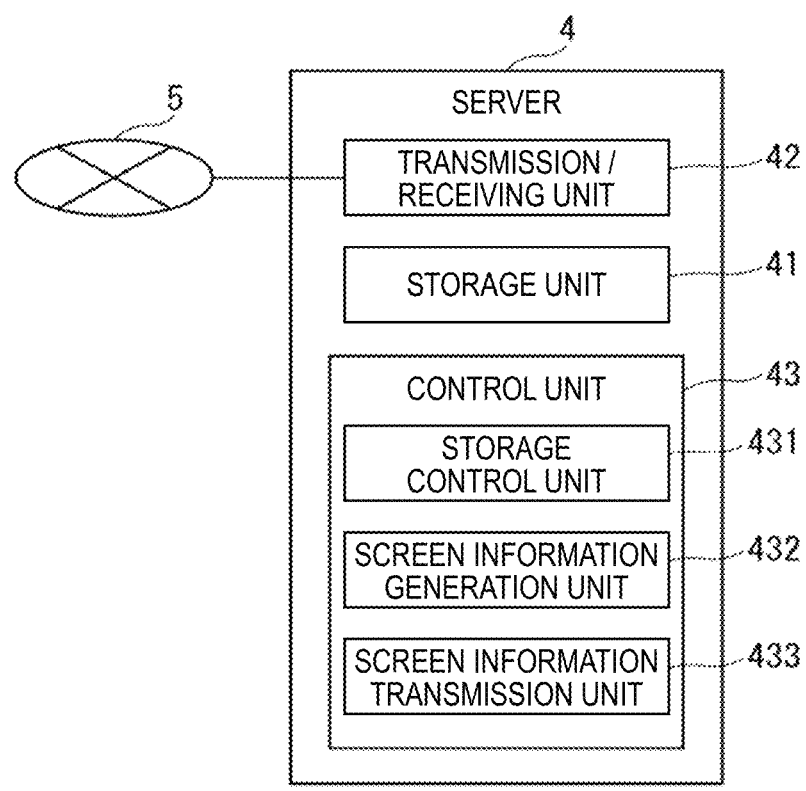
FIG. 8 is a block diagram showing the configuration of a server.

FIG. 8 is a block diagram showing the configuration of the server 4.

The server 4 has a storage unit (server-side storage unit) 41, a transmission/receiving unit 42, and a control unit 43.

The storage unit 41 is made up of an HDD (hard disk drive), flash memory or the like and stores various programs and information that are necessary for the operation of the server 4. The storage unit 41 stores, for example, the pulse rate, the measurement time information, the result of the determination of the state of the user, and the position information transmitted from the mobile information device 3.

The transmission/receiving unit 42 is a communication module which communicates with a terminal device such as a mobile information device or PC (personal computer) via the network 5. The transmission/receiving unit 42 transmits and receives information to and from the terminal device under the control of the control unit 43.

The control unit 43 is configured to control the operation of the server 4 and is made up of a CPU. The control unit 43 functions as a storage control unit (server-side storage control unit) 431, a screen information generation unit 432, and a screen information transmission unit 433 as the CPU executes a program stored in the storage unit 41.

The storage control unit 431 causes the storage unit 41 to store the pulse rate, the measurement time information, the result of the determination of the state of the user and the position information transmitted from the mobile information device 3.

The screen information generation unit 432 generates screen information for displaying a screen showing the pulse rate, the measurement time information, the result of the determination of the state of the user and the position information stored in the storage unit 41.

The screen information transmission unit (server communication unit) 433 transmits the screen information generated by the screen information generation unit 432 to the terminal device.

Transmission Processing by Measurement Apparatus

Figure 9:
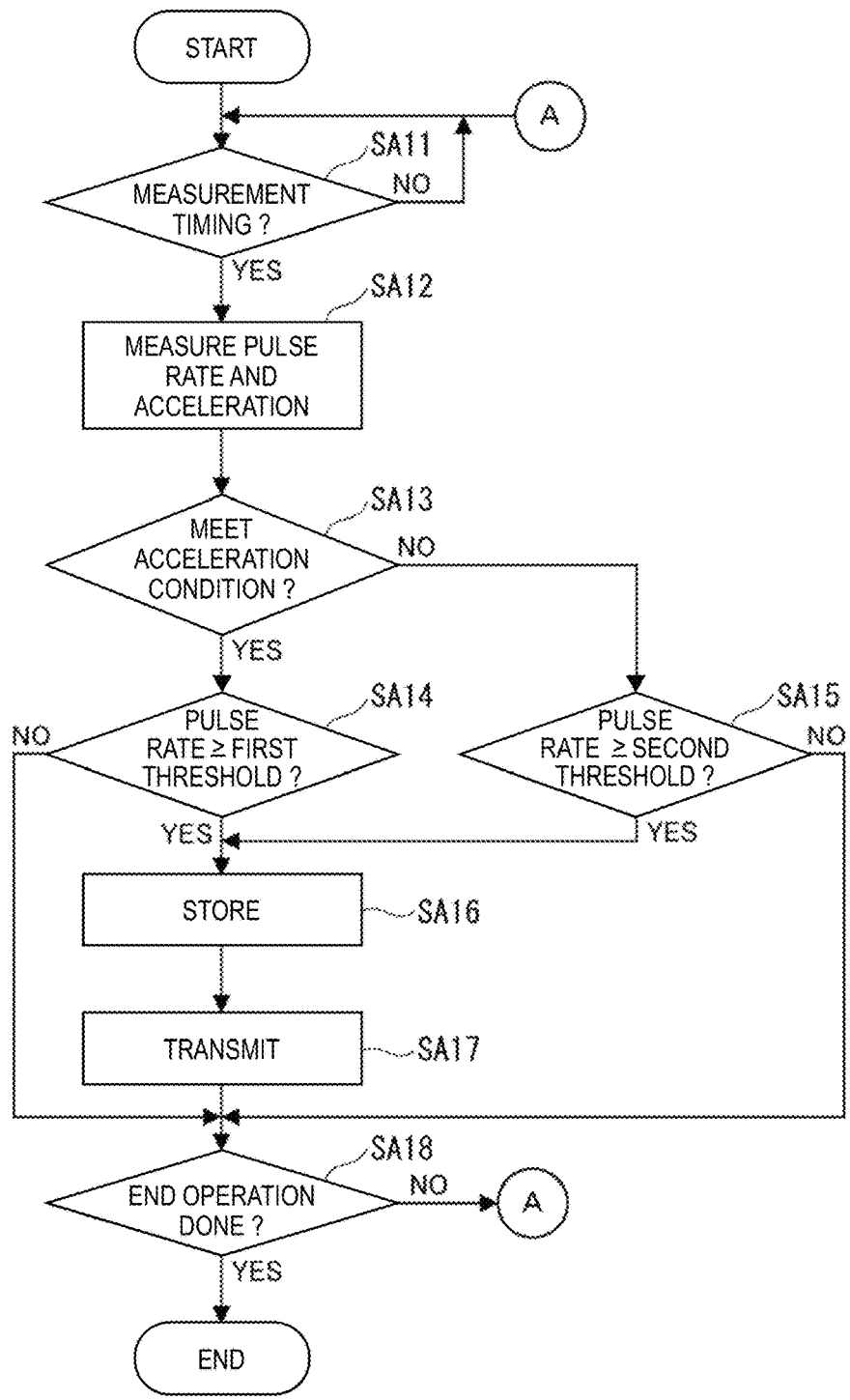
FIG. 9 is a flowchart showing information transmission processing executed by the measurement apparatus.

FIG. 9 is a flowchart showing information transmission processing executed by the measurement apparatus 2.

The control unit 27 determines whether the time measured by the timepiece unit 271 is a measurement timing (i.e. a time at which a measurement should be taken) or not (SA11). The measurement timing is set, for example, every minute. If the determination is NO in SA11, the control unit 27 carries out the determination of SA11 again.

If the determination is YES in SA11, the measurement unit 24 measures a pulse rate and acceleration (SA12).

The acceleration determination unit 275 determines whether the measured acceleration meets a predetermined acceleration condition (SA13). The predetermined acceleration condition is a condition for determining that the user is in a normal active state (not in an exercising state), as described above.

If the determination is YES in SA13 (i.e. the user is not exercising), the first determination unit 2741 determines whether the measured pulse rate is equal to or above a first threshold or not (SA14) (i.e. the user is excited). The first threshold is set to a reference value that enables determination that the user's pulse rate is higher than normal, as described above. The first threshold is set, for example, at 70 beats per minute (70 bpm). If the determination is NO in SA14, the control unit 27 ends the processing.

Meanwhile, if the determination is NO in SA13 (i.e. the user is exercising), the second determination unit 2742 determines whether the pulse rate is equal to or above a second threshold or not (SA15). The second threshold is set to a reference value that enables determination that the user's pulse rate is significantly higher than normal, as described above. The second threshold is set, for example, at 100 beats per minute (100 bpm). If the determination is NO in SA15, the control unit 27 ends the processing.

SA14 and SA15 are sometimes referred to herein as the determination of the biological information.

If the determination is YES in SA14, or if the determination is YES in SA15, the storage control unit 273 causes the storage unit 25 to store the measured pulse rate, the measurement time information and the result of the determination of the state of the user (SA16). SA16 is sometimes referred to herein as the control of the storage.

When SA14 or SA15 yields a "yes" answer, the transmission unit 276 transmits the pulse rate, the measurement time information and the result of the determination of the state of the user (i.e. which step yielded a "yes" answer) stored in the storage unit 25, to the mobile information device 3 (SA17). SA17 is sometimes referred to as the transmission.

As one example, when the user is excited, the pulse rate tends to be higher than normal even though the user is in a normal active state (not exercising). Therefore, in such a case, the determination is YES in SA13 and YES in SA14, and the transmission unit 276 transmits the pulse rate, the measurement time information and the result of the determination of the state of the user (excited state) to the mobile information device 3.

As another example, when the user is exercising vigorously, the pulse rate tends to be significantly higher than normal. Therefore, in such a case, the determination is NO in SA13 and YES in SA15 and the transmission unit 276 transmits the pulse rate, the measurement time information and the result of the determination of the state of the user (vigorously exercising state) to the mobile information device 3.

The control unit 27 determines whether an end operation for the measurement processing is carried out or not, based on an operation signal outputted from the input unit 23 (SA18). If the determination is NO in SA18, the control unit 27 returns the processing to SA11. Meanwhile, if the determination is YES in SA18, the control unit 27 ends the processing.

Storage Processing by Mobile Information Device

Figure 10:
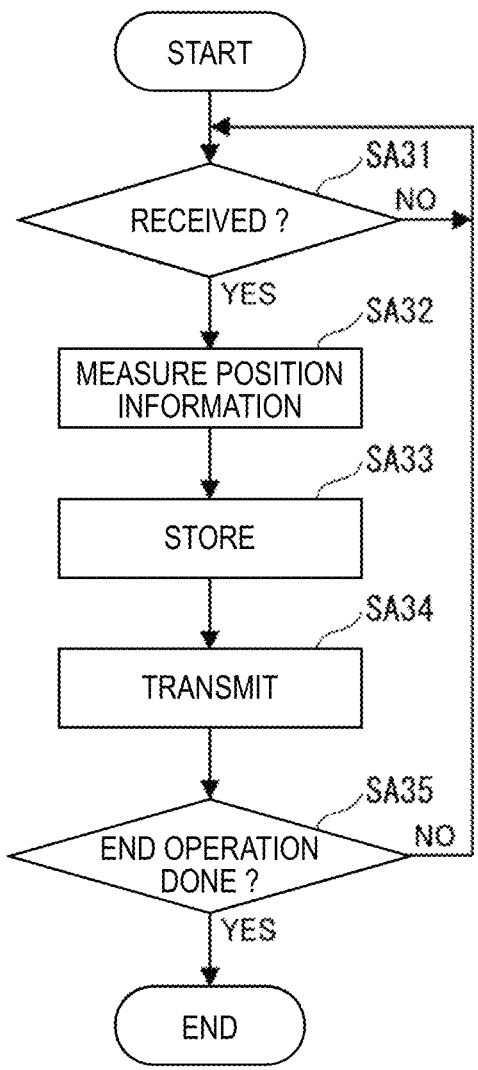
FIG. 10 is a flowchart showing information storage processing executed by the mobile information device.

FIG. 10 is a flowchart showing information storage processing executed by the mobile information device 3.

The control unit 36 determines whether the pulse rate and the measurement time information transmitted from the measurement apparatus 2 are received (SA31). SA31 is sometimes referred to herein as receiving.

If the determination is NO in SA31, the control unit 36 carries out the determination of SA31 again.

If the determination is YES in SA31, the GPS sensor 33 receives a GPS signals and measures the current location of the mobile information device 3 (which is typically the same as the current location of the measurement apparatus 2 and the user) (SA32).

The storage control unit 361 causes the storage unit 34 to store the pulse rate, the measurement time information and the result of the determination of the state of the user transmitted from the measurement apparatus 2, and the position information measured by the GPS sensor 33 (SA33). SA33 is sometimes referred to herein as "the control of the information device-side storage." This step is carried out at the measurement time.

If the pulse rate, the measurement time information and the result of the determination of the state of the user are transmitted from the measurement apparatus 2 not continuously but intermittently (for example, every hour), the measurement of position information by the GPS sensor 33 is periodically carried out and the measured position information is stored in association with time information measured by a timepiece (not shown) provided in the mobile information device 3. When the pulse rate, the measurement time information and the result of the determination of the state of the user are received from the measurement apparatus 2, the stored position information is searched to acquire the position information corresponding to the received measurement time information. The pulse rate, the measurement time information and the result of the determination of the state of the user that are received, and the acquired position information are stored in association with each other in the storage unit 34. Thus, the position information of the measurement apparatus 2 at the measurement time can be stored in the storage unit 34.

Thus, the display control unit 362 can generate an event confirmation screen 37 (FIG. 6) showing the pulse rate, the measurement time information, the result of the determination of the state of the user and the position information stored in the storage unit 34, in response to an operation signal outputted from the input unit 32, and can display the event confirmation screen 37 on the display unit 31. This display process is sometimes referred to herein as "the control of the display."

By browsing the event confirmation screen 37, the user can ascertain the time and place at which the user is in an excited state and the pulse rate at that time, and the time and place at which the user is in a vigorously exercising state and the pulse rate at that time.

The transmission unit 363 transmits the pulse rate, the measurement time information, the result of the determination of the state of the user and the position information stored in the storage unit 34, to the server 4 (SA34).

The control unit 36 determines whether an end operation for the storage processing is carried out, based on an operation signal outputted from the input unit 32 (SA35). If the determination is NO in SA35, the control unit 36 returns the processing to SA31. If the determination is YES in SA35, the control unit 36 ends the processing.

Display Processing by Server

The pulse rate, the measurement time information, the result of the determination of the state of the user and the position information transmitted from the transmission unit 363 to the server 4 are stored in the storage unit 41 by the storage control unit 431.

Here, the pulse rate, the measurement time information, the result of the determination of the state of the user and the position information stored in the storage unit 41 can be browsed on a terminal device such as a mobile information device or PC.

That is, as an information browsing request signal is transmitted from the terminal device to the server 4, the screen information generation unit 432 generates an event confirmation screen information showing the pulse rate, the measurement time information, the result of the determination of the state of the user and the position information stored in the storage unit 41, in response to the browsing request signal.

The screen information transmission unit 433 transmits the generated event confirmation screen information to the terminal device that is the transmission source of the browsing request signal.

Thus, in the terminal device, an event confirmation screen 38 is generated and displayed on the display unit, based on the received event confirmation screen information.

Figure 11:
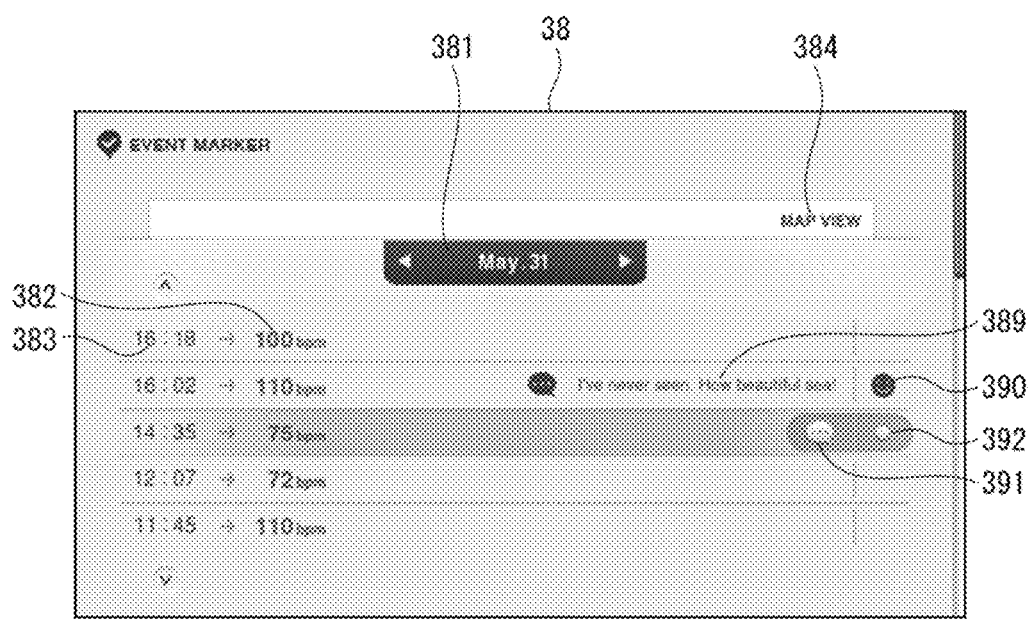
FIG. 11 shows another example of the event confirmation screen.

FIG. 11 shows an example of the event confirmation screen 38 displayed on the display unit of a PC, as an example of a terminal device.

In the event confirmation screen 38, a date 381 when the measurement is carried out, a pulse rate 382 and measurement time information 383 stored in the storage unit 41 of the server 4, and a map information display tab 384 for displaying map information 385 (FIG. 12) indicating position information are shown. While only hours and minutes are shown here as the measurement time information 383, an hour-minute-second indication or an hour-only indication may also be shown.

Figure 12:
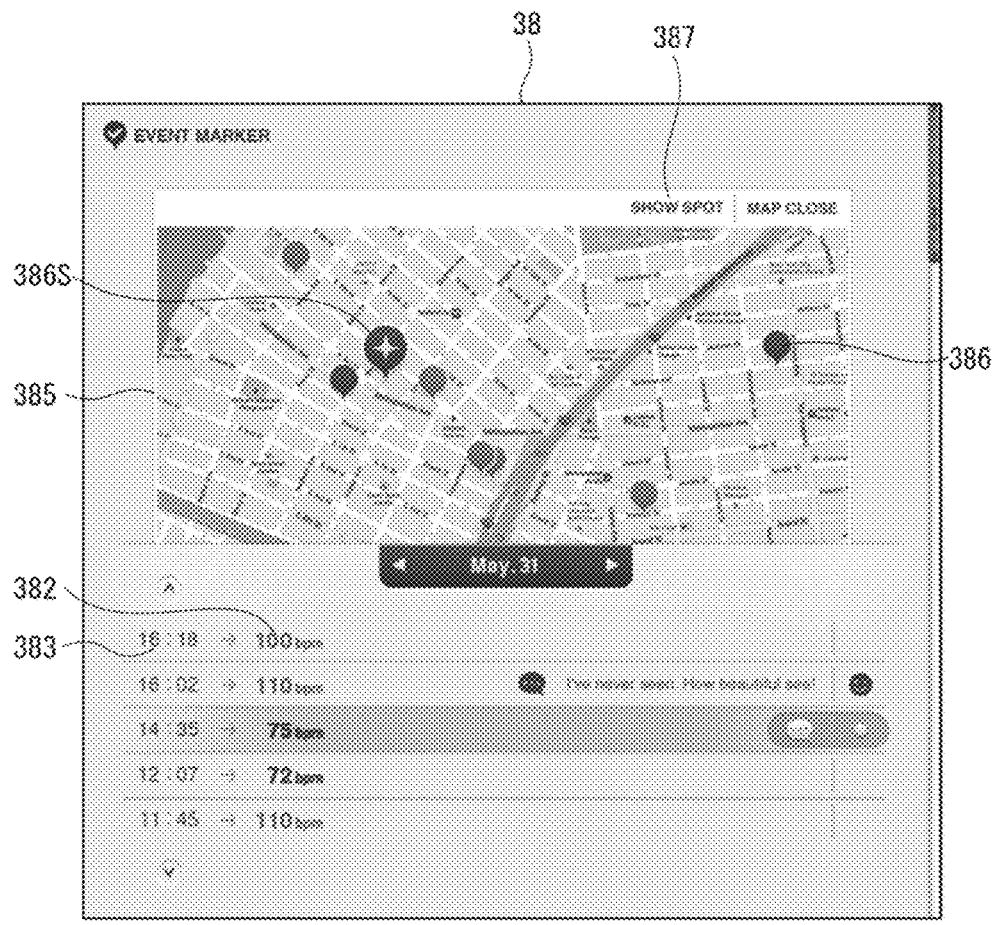
FIG. 12 shows another example of the event confirmation screen.

The pulse rate 382 and the measurement time information 383 are shown in the form of a list by each day when measurement is carried out. As the user operates the input unit to select the map information display tab 384, the map information 385 is displayed, as shown in FIG. 12. In the map information 385, a place indicated by the position information corresponding to the pulse rate 382 and the measurement time information 383 is shown by a marker 386 on a map.

The result of the determination of the state of the user on whether the user is in an excited state or in a vigorously exercising state is expressed, for example, by the color of the pulse rate 382, the measurement time information 383 and the marker 386. For example, an excited state is expressed by a cold color (e.g. green, blue, or purple), and a vigorously exercising state is expressed by a warm color (e.g. red, orange, or yellow).

That is, by browsing the event confirmation screen 38, the user can ascertain the time and place at which the user is in an excited state, and the pulse rate at that time; and the time and place where the user is in a vigorously exercising state, and the pulse rate at that time.

If the user operates the input unit to select one of the pulse rates 382 and the measurement time information 383 from the list, a marker 386S corresponding to the pulse rate 382 and the measurement time information 383 that are selected is shown in an enlarged manner. Thus, the place where the selected pulse rate 382 is measured can be clearly displayed on the map.

Figure 13:
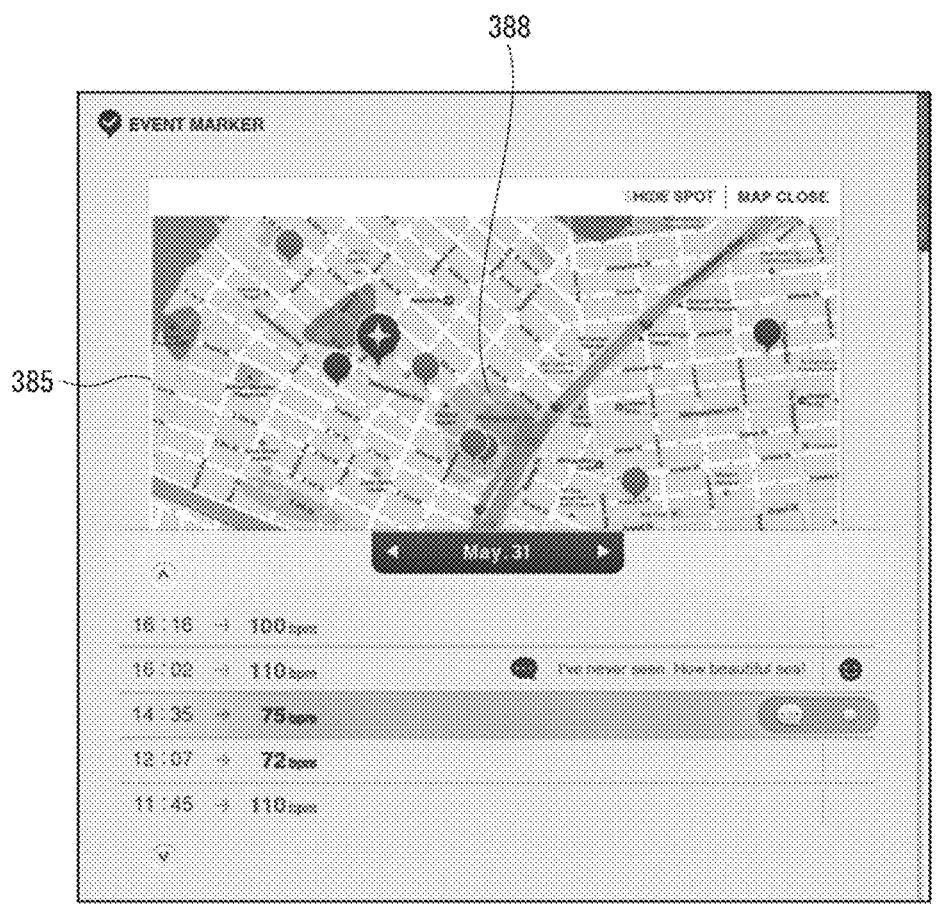
FIG. 13 shows another example of the event confirmation screen.

Also, a spot information display button 387 is shown in the map information 385. As the user operates the input unit to select the spot information display button 387, spot information 388 is displayed, as shown in FIG. 13. The spot information 388 is, for example, information indicating an area where many people are in an excited state or an area where many people are in a vigorously exercising state.

Back to FIG. 11, a comment 389 and an emoticon 390 can be displayed with the pulse rate 382 and the measurement time information 383. The comment 389 and the emoticon 390 can be inputted by the user operating the input unit.

Specifically, as the user operates the input unit to select one of the pulse rates 382 and the measurement time information 383 from the list, a comment input icon 391 and an emoticon input icon 392 are displayed at the right end of the pulse rate 382 and the measurement time information 383 that are selected.

Figure 14:
FIG. 14 shows another example of the event confirmation screen.

Then, as the user operates the input unit to select the comment input icon 391, a comment input section 394 is displayed, as shown in FIG. 14. The user then can input the comment 389 by operating the input unit to input a comment in the comment input section 394.

Figure 15:
FIG. 15 shows another example of the event confirmation screen.

Also, as the user operates the input unit to select the emoticon input icon 392, an emoticon selection image 395 including plural kinds of emoticons is displayed, as shown in FIG. 15. The user then can input the emoticon 390 by operating the input unit to select one of the emoticons.

Thus, the comment and the emotion at the time of measurement can be left as a memo with respect to the pulse rate 382 and the measurement time information 383. In the measurement information management system 1, the inputted comment and emoticon are synchronized between the event confirmation screen 38 and the event confirmation screen 37 displayed on the mobile information device 3.

Sharing of Information

The event confirmation screen 38 can be shared with the user's friends. In this case, the user registers people to share information with on the server 4.

Figure 16:
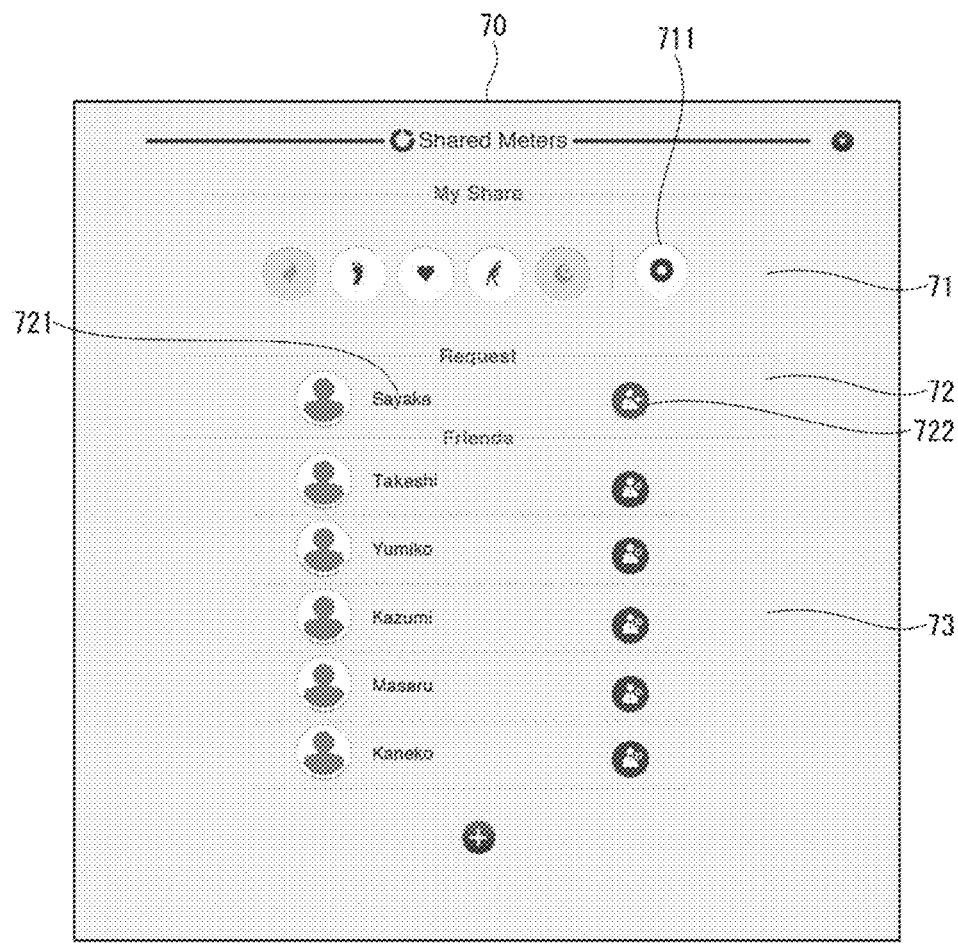
FIG. 16 shows an example of an information sharing setting screen according to an embodiment.

Specifically, the user accesses the server 4 via the terminal device and causes the display unit to display a sharer registration screen 70 shown in FIG. 16. The sharer registration screen 70 can also be displayed on the display unit 31 of the mobile information device 3.

In the sharer registration screen 70, a shared item section 71 showing an item on which information sharing is permitted, a sharing requester section 72 showing another person who is requesting information sharing, and a sharing registered partner section 73 showing those people who are already registered as information sharing partners, are displayed.

In the shared item section 71, an icon 711 indicating the event confirmation screen 38 is shown. In addition, icons indicating the calories burned (flame), number of steps taken (footprint), pulse rate (heart), exercising state (stretching figure), and sleeping state (moon and star) are shown in the shared item section 71.

While determination and storage of calories burned, steps taken, and sleeping state are not described in detail herein, those of ordinary skill in the art will appreciate how to implement these determinations using the measurement apparatus 2 and/or mobile information device 3, and/or by integrating other hardware systems. For example, a separate sleep monitor and/or footstep counter can be synched with the software described herein. Headband-worn sleep monitors such as those formerly manufactured by Zeo, Inc. are generally known in the art, as are wristband- or clothing-worn footstep counters such as those manufactured by FitBit Inc., certain models of which can also track sleep and/or calories burned. These and/or other separate items of hardware can be made to communicate with the apparatuses and systems described herein in ways that can easily be implemented by those of ordinary skill in the art without undue experimentation. Additionally or alternatively, the measurement apparatus 2 and/or mobile information device 3 described herein can be modified to track sleep, calories burned, and/or footsteps taken, in ways that can easily be implemented by those of ordinary skill in the art without undue experimentation.

Figure 17:
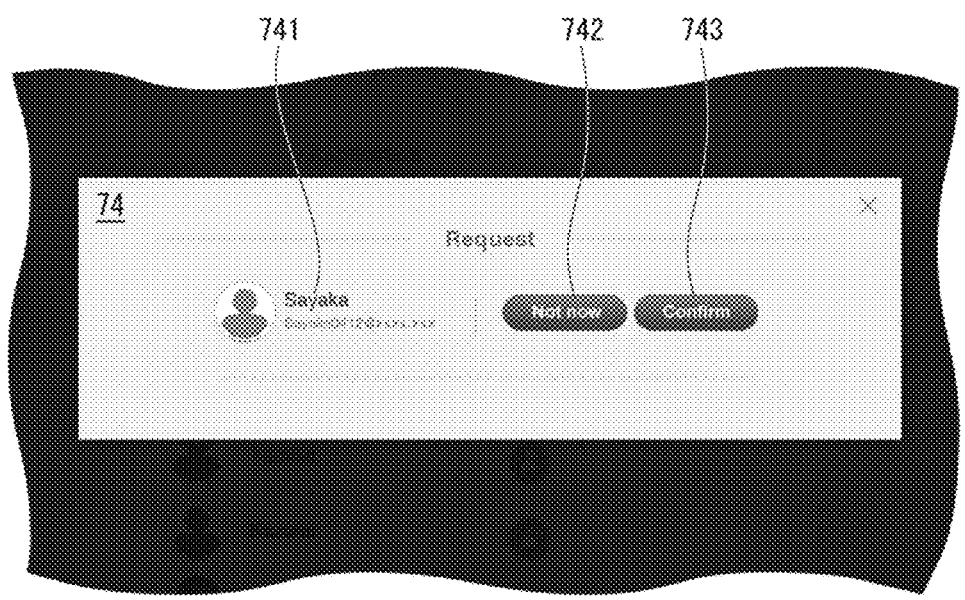
FIG. 17 shows an example of the information sharing setting screen.

In the sharing requester section 72, a registration name 721 of another person who is requesting information sharing and a registration screen display button 722 are shown. As the user operates the input unit to select the registration screen display button 722, a registration screen 74 is displayed, as shown in FIG. 17.

Figure 18:
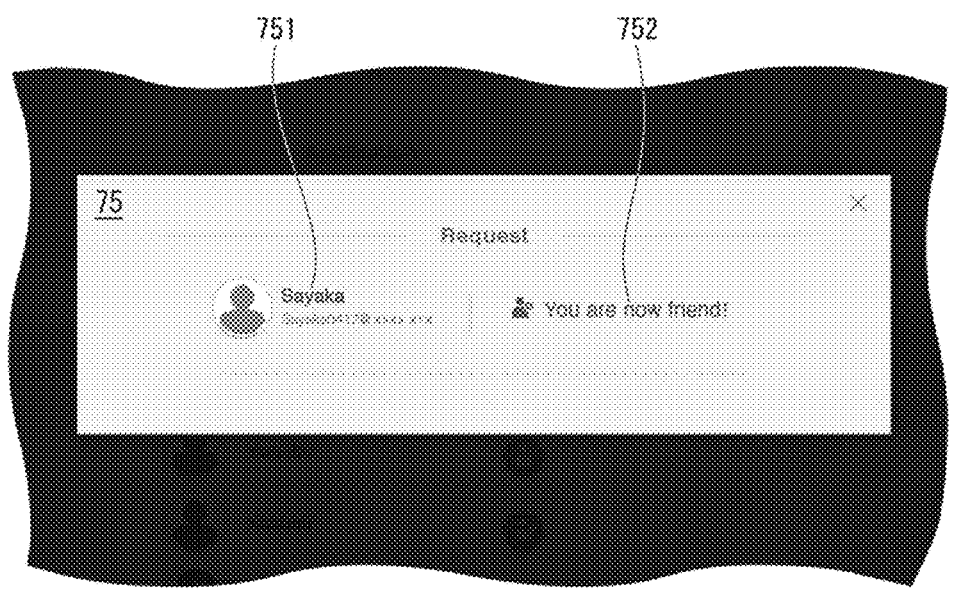
FIG. 18 shows an example of the information sharing setting screen.

In the registration screen 74, a registration name 741, a registration pending button 742, and a registration button 743 are shown. As the user operates the input unit to select the registration button 743, a registration confirmation screen 75 is displayed, as shown in FIG. 18. In the registration confirmation screen 75, a registration name 751 and a registration completion message 752 are shown. Thus, another person who is requesting information sharing can be registered as an information sharing partner.

Also, the user can search through the other people registered in the server 4 to find a partner whom the user wants to request information sharing from, and then request the partner thus searched out to allow registration for information sharing. In this case, as the partner permits the registration, the user can register this partner as an information sharing partner.

Advantages and Effects of Exemplary Embodiments

This embodiments described above have the following advantages and effects.

The user can confirm the times and places at which the user is in an excited state, by browsing the event confirmation screen 37 or the event confirmation screen 38. Thus, the user can learn things with exciting effects, for example, by remembering the actions at these times and places. Then, by referring to this information, the user can make an action plan suitable for the feelings at the time. Moreover, by confirming the places where the user is excited, the user can easily remember places where the user enjoys himself/herself or the like, and can make a plan to visit these places.

Also, the user can confirm the pulse rate when the user is in an excited state, by browsing the event confirmation screen 37 or the event confirmation screen 38.

The storage control unit 273 of the measurement apparatus 2 causes the storage unit 25 to store the pulse rate, the measurement time information, and the result of the determination of the state of the user, if the first determination unit 2741 determines that the pulse rate is equal to or above the first threshold. Thus, the pulse rate, the measurement time information, and the result of the determination of the state of the user when the user is in an excited state can be stored in the storage unit 25 without carrying out complex processing. Therefore, the processing load on the measurement apparatus 2 can be low and the power consumption thereof can be low as well. Particularly if the measurement apparatus 2 is small-sized and driven by a battery, this effect can be outstanding.

The storage control unit 273 of the measurement apparatus 2 causes the storage unit 25 to store the pulse rate and the measurement time information, if the acceleration is determined as meeting the predetermined acceleration condition (YES in SA13) and the pulse rate is equal to or above the first threshold (YES in SA14).

Here, since both the exercising state and the excited state show values larger than the normal resting pulse rate, it is difficult to determine these states, based on the pulse rate only. However, according to the above-described embodiments, when the user is in the exercising state, the pulse rate, the measurement time information, and the result of the determination of the state of the user are not stored in the storage unit 25 even if the pulse rate is equal to or above the first threshold. Therefore, when the user is in the exercising state, storing of the pulse rate, the measurement time information, and the result of the determination of the state of the user in the storage unit 25 due to an erroneous determination that the user is in the excited state, can be prevented. That is, the time when the user is in the excited state can be precisely determined and transmitted to the mobile information device 3.

The mobile information device 3 has the GPS sensor 33. According to this configuration, for example, position information need not be measured in the measurement apparatus 2. Therefore, the processing load on the measurement apparatus 2 can be low and the power consumption thereof can be low as well. Particularly if the measurement apparatus 2 is small-sized and driven by a battery, this effect can be outstanding.

The pulse rate, the measurement time information, the result of the determination of the state of the user, and the position information are stored and accumulated in the storage unit 41 of the server 4. Therefore, the user can share the information with other people having the user's permission to browse. Also, by analyzing the pulse rate, the measurement time information, the result of the determination of the state of the user, and the position information that are stored in the storage unit 41, the following effects can be achieved.

For example, at a movie theater or concert venue, if plural members of the audience use the measurement apparatus 2, exciting moments or the like can be statistically analyzed. At an exhibition site, if plural visitors use the measurement apparatus 2, showpieces (exhibition facilities) in which visitors take interest or time brackets in which visitors take interest in these showpieces can be statistically analyzed. At an amusement park, if plural visitors use the measurement apparatus 2, attractions which excite visitors or time brackets in which visitors become excited can be statistically analyzed. Also, inside a retail shop, if plural customers use the measurement apparatus 2, products (product racks) in which customers take interest or time brackets in which customers take interest in these products can be statistically analyzed. Moreover, if plural car drivers use the measurement apparatus 2, places and time brackets in which drivers are in an excited state while driving, that is, places and time brackets in which accidents are likely to occur can be statistically analyzed.

The event confirmation screen 37 is displayed on the display unit 31 in response to an operation signal outputted from the input unit 32. Therefore, for example, when another information is displayed on the display unit 31, the event confirmation screen 37 can be prevented from being displayed on the display unit 31 against the user's intention. Thus, usability of the mobile information device 3 can be improved.

Other Embodiments

The invention is not limited to the configurations of the above-described embodiments and various modifications can be carried out within the scope and spirit of the appended claims.

For example, while the measurement unit 24 measures pulse rates as one example of "biological information" in the above-described embodiments, other information such as heart rate, pulse waves, brain waves, blood pressure, or electrodermal response, for example, may additionally or alternatively be measured. Also, while the measurement unit 24 measures acceleration as one example of "exercise information," other information such as angular velocity or vibrations, for example, may additionally or alternatively be measured.

In the above-described embodiments, the measurement time information is hour-minute-second information indicating the measurement time when the pulse rate is measured. However, the measurement time information may also be hour-minute-only information omitting seconds, or may be hour-only information (on the hour) omitting minutes and seconds. Also, in the case of hour-minute-second information, the expression of seconds may be changed, for example, to every five seconds, every ten seconds, every thirty seconds or the like. In the case of hour-minute information, the expression of minutes may be changed to every five minutes or the like.

In the above-described embodiments, the storage control unit 361 causes the storage unit 34 to store the position information measured by the GPS sensor 33 at the same time as the measurement time indicated by the measurement time information transmitted from the measurement apparatus 2. However, if there is no position information measured at that time, position information measured by the GPS sensor 33 at the closest time to the measurement time indicated by the measurement time information or at a time within a predetermined time range from the measurement time may be stored in the storage unit 34.

In the above-described embodiments, in the measurement apparatus 2, the pulse rate, the measurement time information, and the result of the determination of the state of the user are transmitted to the mobile information device 3 if the user is determined as being in an excited state. However, the pulse rate, the measurement time information, and the result of the determination of the state of the user may also be transmitted to the mobile information device 3 if the user is determined as being in a comfortable state (relaxed state). Whether or not the user is in a comfortable state can be determined, for example, by analyzing the degree of activity of sympathetic nerves, the balance between sympathetic nerves and parasympathetic nerves, or the like, using a pulse wave sensor and based on the result of measurement by the pulse wave sensor. Specifically, the comfortable state can be determined, based on the proportion of high-frequency components (HF) and low-frequency components (LF) of the pulse wave.

In the above-described embodiments, the position information of the current location of the measurement apparatus 2 is measured by the GPS sensor 33 of the mobile information device 3. However, the invention is not limited to this. For example, a GPS sensor may be provided in the measurement apparatus 2 and the position information of the measurement apparatus 2 may be measured by this GPS sensor. In this case, the measured position information may be stored in the storage unit 25 by the storage control unit 273, along with the pulse rate, the measurement time information, and the result of the determination of the state of the user. The pulse rate, the measurement time information, the result of the determination of the state of the user, and the position information stored in the storage unit 25 are transmitted to the mobile information device 3 by the transmission unit 276. The GPS sensor 33 is one example of a position sensor. A different satellite positioning system, such as GLONASS or Galileo, or a non-satellite-based positioning system may be used.

If a GPS sensor is provided in the measurement apparatus 2, for example, the position information need not be measured in the mobile information device 3 and therefore the processing load on the mobile information device 3 can be low. Thus, in the mobile information device 3, disturbance of execution of other processing can be avoided and usability can be improved. Moreover, the user only has to wear the measuring apparatus 2 when exercising, and does not need to hold the mobile information device 3 while exercising. Therefore, the user can exercise more easily than in the case where the user holds both the measurement apparatus 2 and the mobile information device 3 while exercising.

Also, approximate position information of the measurement apparatus 2 may be measured, based on the position information of a base station of a mobile telephone network with which the mobile information device 3 communicates wirelessly or of an access point of the network 5.

In the above-described embodiments, the measurement information management system 1 includes the measurement apparatus 2, the mobile information device 3, and the server 4. However, the measurement information management system need not include the mobile information device 3. In this case, the pulse rate, the measurement time information, and the result of the determination of the state of the user are transmitted from the measurement apparatus 2 to the server 4 via the network 5. In this case, for example, a GPS sensor is provided in the measurement apparatus 2 and the position information of the current location of the measurement apparatus 2 is measured by this GPS sensor, as described above. Also, approximate position information of the measurement apparatus 2 may be measured, based on the position information of an access point of the network 5 with which the measurement apparatus 2 wirelessly communicates.

While the measurement apparatus 2 has the acceleration sensor 242 in the above-described embodiments, the acceleration sensor 242 can be omitted. For example, if the measurement apparatus 2 is used only when the user in the normal active state or the like, the excited state can be determined on the basis of the pulse rate only, without having to measure acceleration. Therefore, the acceleration sensor 242 can be omitted.

In the above-described embodiments, whether the pulse rate is equal to or above the first threshold is determined in SA14 and whether the pulse rate is equal to or above the second threshold is determined in SA15. However, for example, if only the excited state is to be confirmed or if only the vigorously exercising state is to be confirmed, or the like, only one of SA14 and SA15 may be carried out.

In the above-described embodiments, the pulse rate, the measurement time information, and the map information are shown in the event confirmation screens 37, 38. However, in other embodiments, only the measurement time information and/or the map information is shown.

While the mobile information device 3 is used in the above-described embodiments, a stationary information device such as desktop PC may be used instead of the mobile information device 3.

In the above-described embodiments, wireless connection is provided between the measurement apparatus 2 and the mobile information device 3 and between the mobile information device 3 and the network 5. However, wired connection may also be used.

As will be understood by those skilled in the art, the present invention may be embodied in other specific forms without departing from the essential characteristics thereof. Many other embodiments are possible without departing from the essential characteristics thereof. Many other embodiments are possible without deviating from the spirit and scope of the invention. These other embodiments are intended to be included within the scope of the present invention, which is set forth in the following claims.

What is claimed is:

1. A measurement apparatus, comprising:
a storage unit;
a timepiece unit which measures time;
a biological information measurement unit which measures biological information indicative of a state of a user;
a biological information determination unit which determines whether the biological information meets one of one or more predetermined biological information conditions to thereby determine whether or not the state of the user is one of one or more predetermined states;
a storage control unit which, in response to determining that the biological information meets one of the predetermined biological information conditions and determining that the state of the user is one of the predetermined states, causes the storage unit to store a measurement time at which the biological information is measured; and
a transmission unit which transmits transmission information comprising the stored measurement time and the stored biological information that is measured at the measurement time, wherein, when the biological information is determined to not meet one of the predetermined biological information conditions, the biological information is not stored or transmitted.

2. The apparatus of claim 1, further comprising a position information measurement unit which measures a location of the measurement apparatus, wherein the transmission information further comprises the location of the measurement apparatus at the measurement time.

3. The apparatus according to claim 1, wherein the biological information comprises a pulse rate, and the predetermined biological information condition comprises the pulse rate being equal to or above a predetermined threshold.

4. The apparatus according to claim 1, wherein the predetermined states comprise at least one member of the group consisting of: an exercising state of the user, a non-exercising state of the user, a non-vigorously exercising state of the user, and a vigorously exercising state of the user.

5. The apparatus according to claim 1, wherein the biological information comprises a pulse rate and information indicative of whether or not the user is exercising, and one of the predetermined biological information conditions comprises the pulse rate being equal to or above a predetermined threshold when the user is not exercising, and the predetermined state of the user comprises an excited state.

6. The apparatus according to claim 1, further comprising a server,
wherein the transmission unit transmits the transmission information to an information device via the server;
wherein the server comprises:
a server-side storage unit which stores the transmission information; and
a server communication unit which provides the transmission information, based on a request by the information device.

7. The apparatus according to claim 1, comprising an accessory configured to be worn by the user.

8. The apparatus according to claim 1, wherein the biological information measurement unit comprises a pulse rate monitor.

9. The apparatus according to claim 1, wherein the biological information measurement unit comprises an accelerometer.

10. A measurement information management method for a measurement information management system, the system comprising a measurement apparatus comprising: a storage unit, a timepiece unit which measures time, and a biological information measurement unit which measures biological information indicative of a state of a user; and an information device communicating with the measurement apparatus and comprising an information device-side storage unit and a display unit; wherein the information device further comprises a position information measurement unit which measures a location of the position information measurement unit; the method comprising:
determining whether the biological information meets one of one or more predetermined biological information conditions to thereby determine whether or not the state of the user is one of one or more predetermined states;
storing, in the storage unit, in response to determining that the biological information meets one of the predetermined biological information conditions and determining that the state of the user is one of the predetermined states, a measurement time at which the biological information is measured;
transmitting transmission information from the measurement apparatus to the information device, the transmission information comprising the measurement time and the biological information that is measured at the measurement time, wherein when the biological information is determined to not meet one of the predetermined biological information conditions the biological information is not stored or transmitted by the measurement apparatus;
storing, in the information device-side storage unit, the measurement time and the location; and
simultaneously displaying, in the display unit, the measurement time and the location corresponding to the measurement time with an indication on a displayed map.

11. The method according to claim 10, wherein the biological information comprises a pulse rate, and the predetermined biological information condition comprises the pulse rate being equal to or above a predetermined threshold.

12. The method according to claim 10, wherein the one or more predetermined states comprise at least one member of the group consisting of: an exercising state of the user, a non-exercising state of the user, a non-vigorously exercising state of the user, and a vigorously exercising state of the user.

13. The method according to claim 10, wherein the biological information comprises a pulse rate and information indicative of whether or not the user is exercising, and one of the predetermined biological information conditions comprises the pulse rate being equal to or above a predetermined threshold when the user is not exercising, and the predetermined state of the user comprises an excited state.

* * * * *